(12) United States Patent
Niznick

(10) Patent No.: US 7,785,107 B2
(45) Date of Patent: Aug. 31, 2010

(54) MULTI-FUNCTIONAL FIXTURE MOUNT

(76) Inventor: Gerald A. Niznick, 3993 Howard Hughes Pkwy., #540, Las Vegas, NV (US) 89109

( * ) Notice: Subject to any disclaimer, the term of this patent is extended or adjusted under 35 U.S.C. 154(b) by 101 days.

(21) Appl. No.: 11/047,960

(22) Filed: Feb. 1, 2005

(65) Prior Publication Data
US 2006/0172257 A1 Aug. 3, 2006

(51) Int. Cl.
*A61C 8/00* (2006.01)
(52) U.S. Cl. ..................................... 433/173
(58) Field of Classification Search ................ 433/173, 433/174
See application file for complete search history.

(56) References Cited

U.S. PATENT DOCUMENTS

| 5,947,732 | A * | 9/1999 | Beaty et al. ................. 433/172 |
| 6,464,500 | B1 * | 10/2002 | Popovic ...................... 433/173 |
| 6,508,650 | B2 * | 1/2003 | Gittleman ................... 433/172 |
| 6,824,386 | B2 * | 11/2004 | Halldin et al. .............. 433/173 |
| 6,951,462 | B2 * | 10/2005 | Kumar et al. ............... 433/174 |
| 7,014,464 | B2 * | 3/2006 | Niznick ...................... 433/173 |
| 7,137,816 | B2 * | 11/2006 | Gervais et al. ............. 433/173 |
| 7,699,613 | B2 * | 4/2010 | Niznick ...................... 433/174 |
| 2003/0054319 | A1 * | 3/2003 | Gervais et al. ............. 433/173 |
| 2003/0228556 | A1 * | 12/2003 | Giorno ........................ 433/174 |
| 2004/0101808 | A1 * | 5/2004 | Porter et al. ................ 433/173 |
| 2005/0233281 | A1 * | 10/2005 | Gittleman ................... 433/173 |
| 2005/0287496 | A1 * | 12/2005 | Niznick ...................... 433/173 |

* cited by examiner

*Primary Examiner*—Ralph A Lewis
(74) *Attorney, Agent, or Firm*—Patrick F. Bright

(57) ABSTRACT

Endosseous dental implants include external threads, and, within an internal passage inside the body of the implant, a lead-in bevel, 8-sided abutment-engaging surfaces, distally positioned 6-sided wrench-engaging surfaces, and internal threading distal to both the 8-sided and 6-sided surfaces, and fixture mounts and abutments including male projections to engage the 6-sided wrench-engaging surfaces inside the implants.

2 Claims, 5 Drawing Sheets

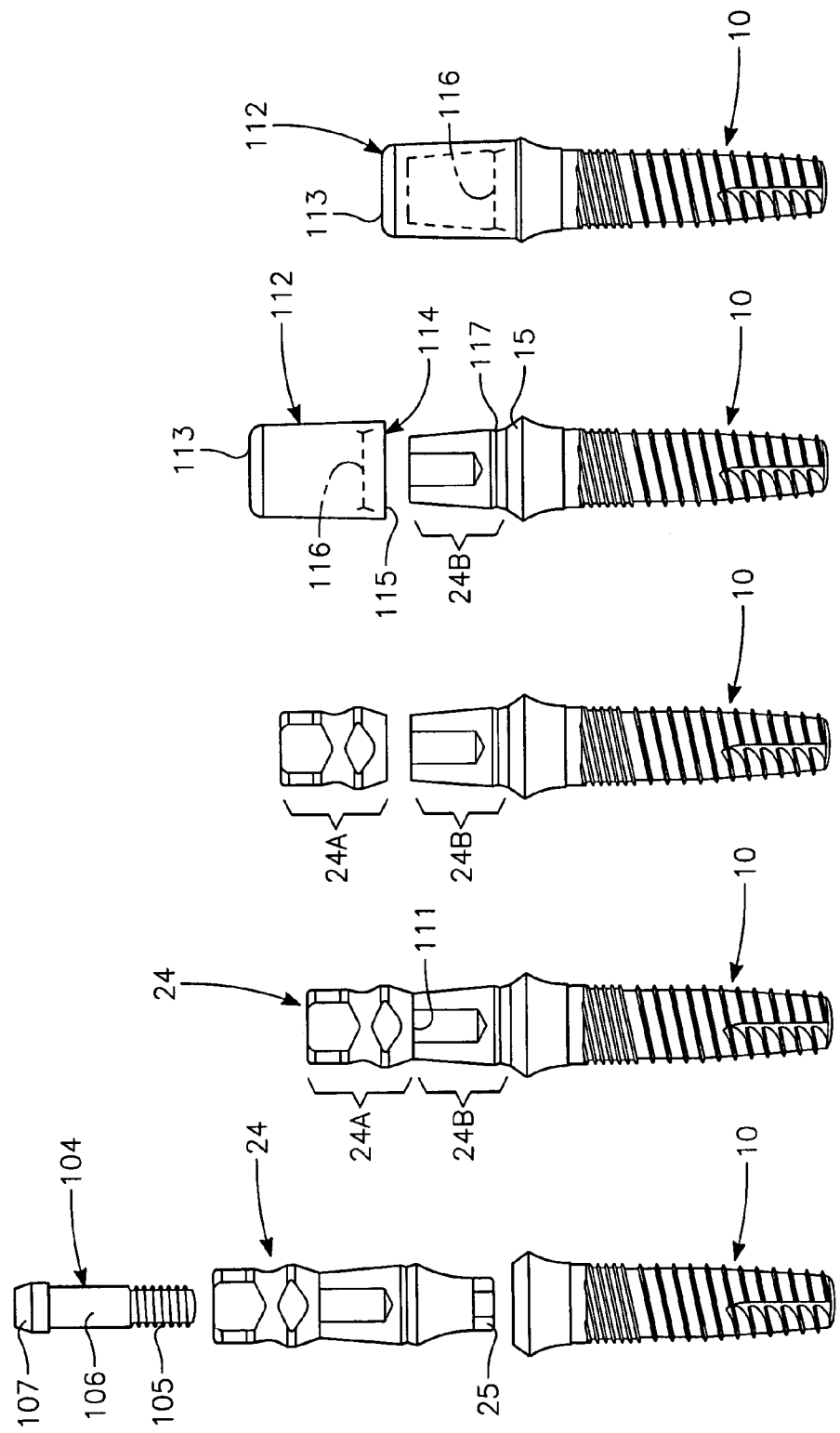

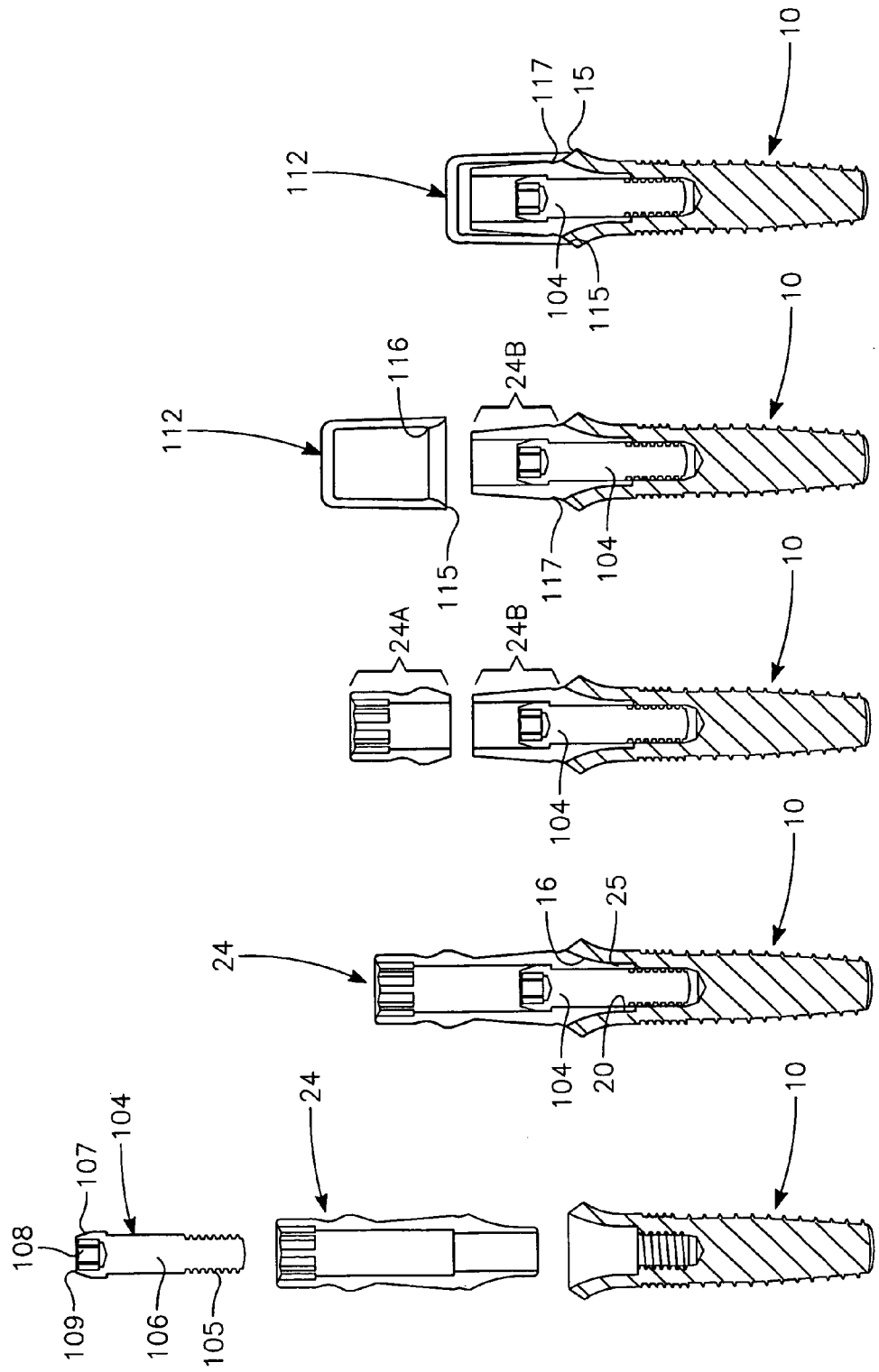

MULTI-FUNCTIONAL FIXTURE MOUNT

This invention relates to externally-threaded endosseous dental implants including an elongated externally-threaded body. The body may include an external self-tapping cutting portion and external multiple lead threads. The proximal end of these implants includes an outwardly tapering unthreaded portion, an opening to an internally-threaded passage that extends distally inside the body from this opening, and a flat or tapered shoulder around this opening. This passage may include a lead-in bevel/chamfer near the opening to the passage, abutment-engaging surfaces and fixture mount-engaging surfaces inside, and near to the opening to the internal passage.

This invention also relates to two-part abutments and to two-part fixture mounts for use with these and other implants. The abutments may include, at their distal end, a multi-sided, e.g., 8-sided, distally extending male portion and, proximal to the 8-sided distal portion, an external bevel/chamfer extending around the proximal end of the 8-sided portion of size and shape sufficient to fit into a lead-in bevel inside the opening to the internal passage of the implants and seat on the tapered shoulder around the opening to the internally threaded shaft. The abutments include a longitudinal passage to receive a fixation screw to fasten the abutment to the implant. The proximal portion of these abutments is frusto-conical, may be straight or angled and may include a wholly or partly circumferential groove for engaging a wholly or partly circumferential protrusion on the inner surface of a snap-on plastic or nylon transfer or comfort cap.

The fixture mounts comprise a multi-sided, e.g., a 6-sided male distal portion, and a bevel/chamfer extending around the proximal end of the 6-sided portion, and of size and shape sufficient to fit into, and seat in a lead-in bevel inside the opening to the internal passage of the implants. The middle portion of the fixture mount comprises a frusto-conical portion that includes a wholly or partly circumferential groove for engaging a wholly or partly circumferential protrusion on the inner surface of a snap-on plastic or nylon transfer or comfort cap. The proximal end of these mounts include external, internal or both external and internal wrench-engaging surfaces to twist, turn or hold the mount and thereby the implant attached to the distal portion of the mount by a fixation screw passing through an internal, longitudinal passage in the mount.

Both the fixture mounts and the abutments include an internal, longitudinal passage to receive a screw, such as a fixation screw, or other fastener that includes a threaded shank and a proximal head or other structure to engage the proximal end of the abutment or fixture mount, or to engage a flange formed on the internal surface of the passage inside the fixture mount or abutment.

The implants may include, in the internal passage of the implant, a proximal lead-in bevel/chamfer, internal 8-sided abutment-engaging surfaces distal to the lead-in bevel/chamfer, and, distal to the 8-sided abutment engaging surfaces, internal 6-sided fixture mount-engaging/abutment-engaging surfaces of sufficient size to accept and engage two-part abutments and two-part fixture mounts. The 6-sided surfaces are smaller in cross-sectional area than the 8-sided surfaces. The internal threads of the internally-threaded passage are distal to both the 8-sided internal abutment engaging surfaces and to the 6-sided internal fixture mount-engaging surfaces, and are smaller in cross-sectional area than the 6-sided surfaces.

These implants may also include one or more of the features of the endosseous dental implants, abutments and other related products, disclosed in the following U.S. patent applications:

Tapered Endosseous Dental Implants With External Multiple Lead Threads (D9473), U.S. patent application Ser. No. 11/047,959, filed on Feb. 1, 2005;

One-Piece, Screw-Receiving, Externally-Threaded Endosseous Dental Implants And Related Transfer Components, Comfort Caps And Abutments (D9470), U.S. patent application Ser. No. 11/056,578, filed on Feb. 11, 2005;

Endosseous Dental Implant (D9462), U.S. patent application Ser. No. 10/877,460, filed Jun. 25, 2004, now U.S. Pat. No. 7,108,510;

Endosseous One-Piece Screw-Type Dental Implants (D9456), U.S. patent application Ser. No. 10/883,275, filed Jul. 1, 2004;

Multi-Part Abutment And Transfer Cap For Use With An Endosseous Dental Implant With Non-Circular, Beveled Implant Abutment Interface (D9452), U.S. patent application Ser. No. 10/741,023, filed Dec. 19, 2003, now U.S. Pat. No. 7,014,464 now abandoned;

U.S. patent application Ser. No. 10/741,061, filed Dec. 19, 2003, entitled "Endosseous Dental Implant" (D9443), now abandoned; and Screw-Type Dental Implant Anchor [0013], U.S. Pat. No. 4,960,381, issued Oct. 2, 1990.

BRIEF DESCRIPTION OF THE DRAWINGS

The implants, abutments and fixture mounts can better be understood by reference to the drawings in which:

FIG. 4 is a side elevation view of the implant, fixture mount and fastener shown in FIG. 2;

FIG. 4A is a side elevation view of the implant and fixture mount shown in FIG. 4, with the fixture mount in place atop the implant;

FIG. 4B is a side elevation view of the implant and fixture mount of FIG. 4A, with the proximal portion of the fixture mount separated from its distal portion;

FIG. 4C shows the dental implant and fixture mount of FIG. 4B, with the proximal portion of the fixture mount discarded, and with a comfort cap positioned above the implant/fixture mount assembly;

FIG. 4D shows the assembly of FIG. 4C, with the comfort cap in place atop the implant;

FIG. 5 shows a side elevation view, in cross-section of the implant/fixture mount/fastener assembly shown in FIG. 4;

FIG. 5A shows a side elevation view, in cross-section, of the fixture mount in place atop the implant, as shown in FIG. 4A;

FIG. 5B shows a side elevation view, in cross-section, of the implant/fixture mount assembly of FIG. 4B, with the proximal portion of fixture mount separated from the distal portion;

FIG. 5C shows a side elevation view, in cross-section, of the implant/fixture mount assembly of FIG. 4C, with the comfort cap positioned above the implant/fixture mount assembly;

FIG. 5D shows a side elevation view, in cross-section, of the comfort cap/fixture mount/fastener assembly of FIG. 4D, and vertical cross-section;

DETAILED DESCRIPTION OF THE DRAWINGS

Figure 1:
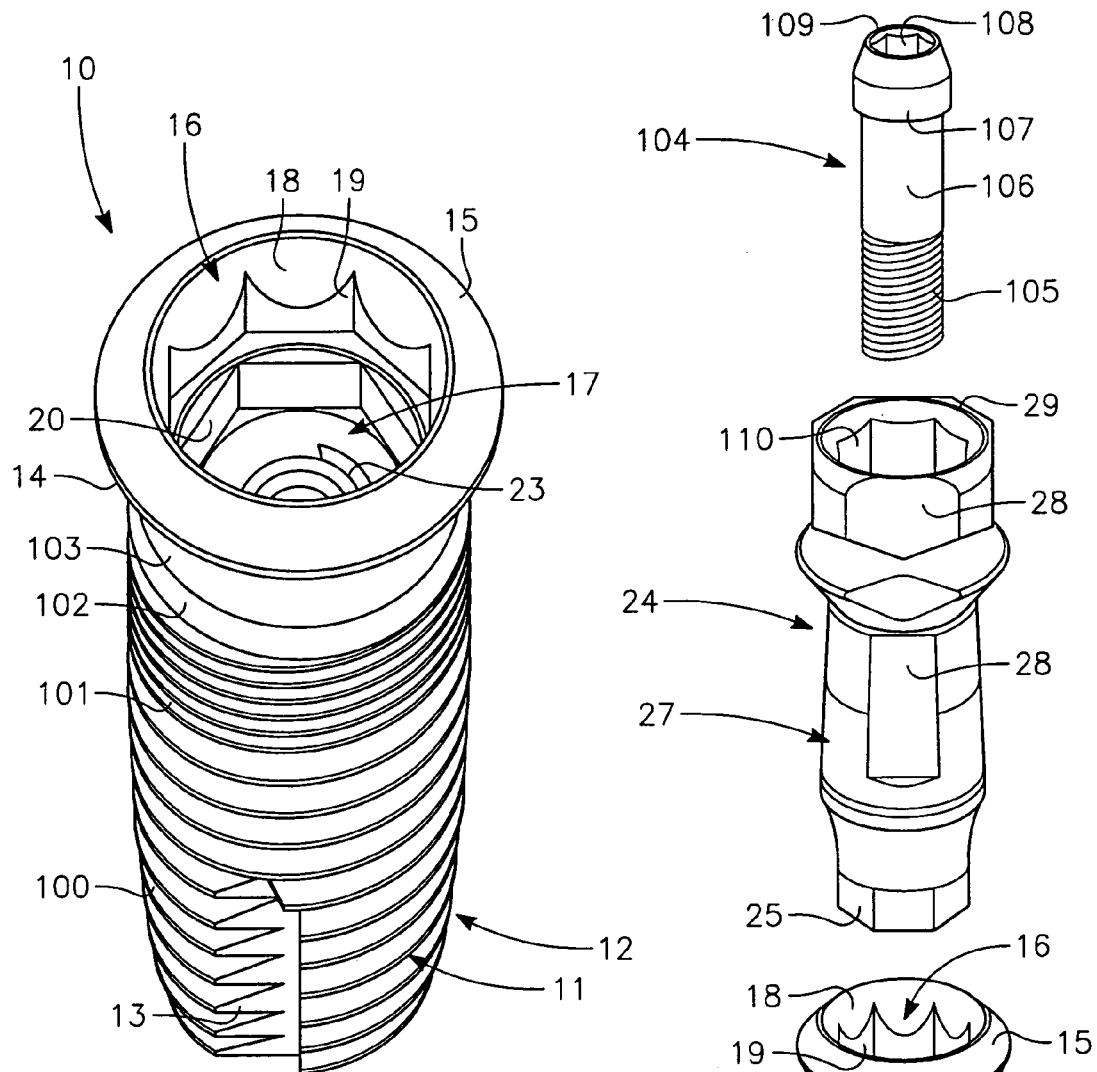
FIG. 1 is a perspective view of an externally-threaded endosseous dental implant with internal abutment-engaging and fixture mount-engaging surfaces.

FIGS. 1, 2, 3A, and 3B show a perspective view of an externally-threaded endosseous dental implant 10. Implant 10 includes a body 12 with external threads 11, and, near the distal end of implant 10, a self-tapping cutter 13. Threads 11 are double lead threads in distal external region 100, and quadruple lead threads in proximal external region 101. Proximal to region 101 are unthreaded cylindrical portion 102, and, outwardly proximally-flared portion 103. Outwardly-flaring, unthreaded portion 14, includes outwardly, distally flaring flat shoulder 15, which extends around opening 16 to internal passage 17. Opening 16 includes lead-in bevel 18. Distal to lead-in bevel 18 is 8-sided female wrench-engaging surfaces 19, adapted to engage an 8-sided male portion on the distal end of a fixture mount or abutment. Distal to surfaces 19 is 6-sided female wrench-engaging surfaces 20, adapted for engaging an insertion tool or a male 6-sided distal projection on an abutment. Distal to both 8-sided wrench-engaging surfaces 19 and 6-sided wrench-engaging surfaces 20 are internal threads 23. These internal threads extend distally inside of, and terminate inside implant 10.

Figure 2:
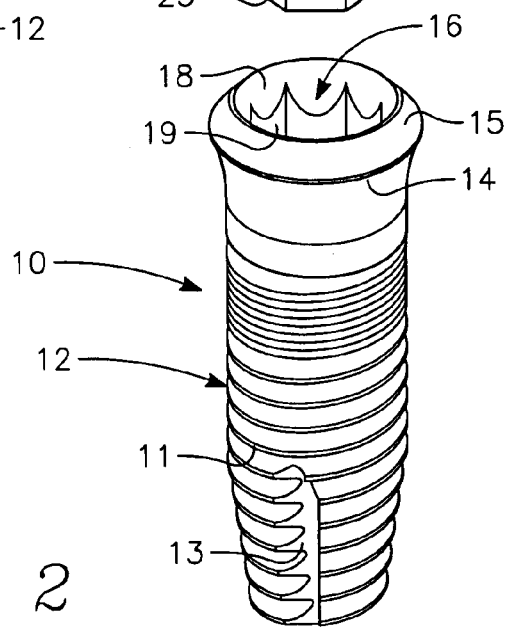
FIG. 2 is a perspective view of the dental implant of FIG. 1, and, positioned above this implant, a perspective view of a fixture mount and a fastener for use with this implant.

FIG. 2 shows fixture mount 24 above dental implant 10, with distal, male, 8-sided projection 25 engaging internal wrench-engaging surfaces 19. Fixture mount 24 includes an internal, longitudinally-extending passage 110 through which threaded fastener 104 can be inserted. The threaded shank 105 of fastener 104 extends distal to wrench-engaging male portion 25, into internal passage 17 in implant 10, where threaded shank 105 engages internal threads 23 in implant 10. A head or other structure atop fastener 104 engages the top surface 29 of fixture mount 24 to hold fixture mount 24 in place atop implant 10.

Figure 3A:
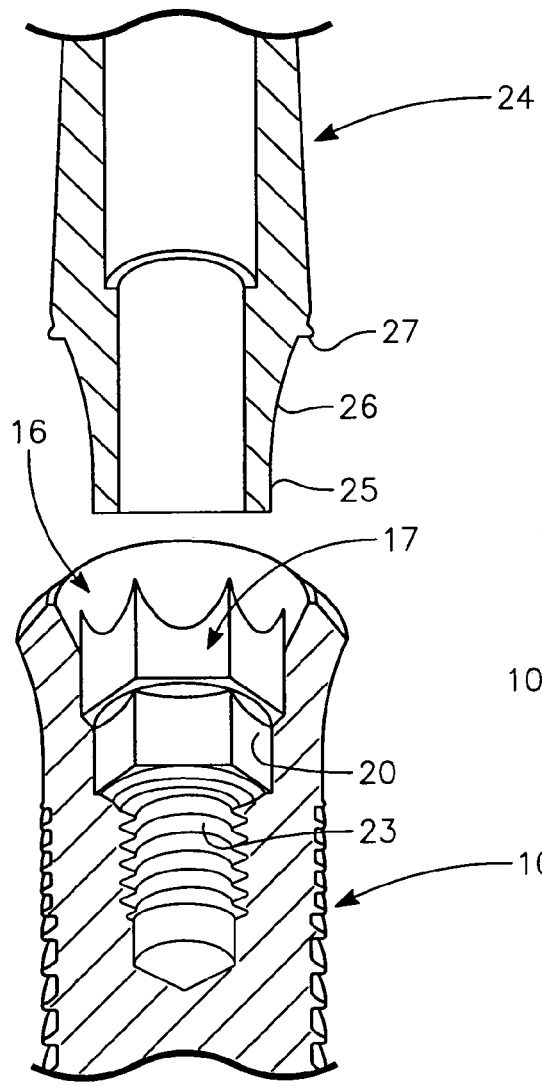
FIG. 3A is a side elevation view of the implant of FIG. 3, with the fixture mount of FIG. 3 in place atop the implant.
Figure 3B:
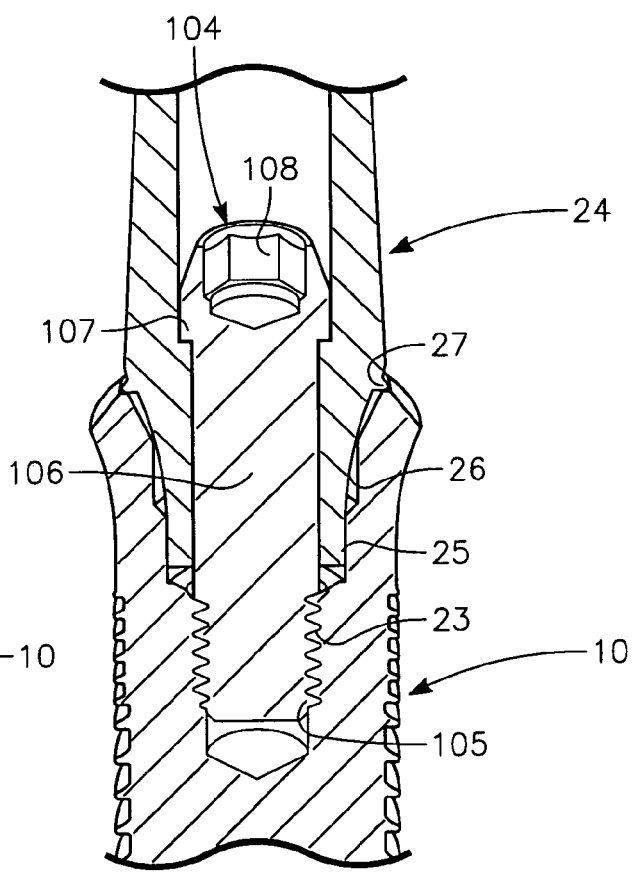
FIG. 3 is a side elevation view, in partial cross-section, of the implant of FIG. 1, and the fixture mount of FIG. 2, positioned above the implant.

FIGS. 3A and 3B show dental implant 10 in partial cross-section, exposing the internal threads 23 inside passage 17. Positioned above implant 10 in FIG. 3A is fixture mount 24. Fixture mount 24 includes, at its distal end, 6-sided male projection 25. Proximal to 6-sided distal portion 25 is bevel/chamfer 26, which extends wholly or partly around fixture mount 24. Proximal to bevel/chamfer 26 is proximal portion 27, which is frusto-conical in shape and includes one or more flat surfaces 28, to facilitate holding, twisting and turning of fixture mount 24.

FIGS. 2 and 3B show fastener 104, which includes threaded distal shank 105 and unthreaded proximal shank portion 106. Atop shank portion 106 is head section 107, which includes internal, wrench-engaging surfaces 108 and lead-in bevel 109 at the proximal end of fastener 104.

FIG. 4A shows fixture mount 24 in place atop implant 10, and fastener 104 in place within passage 110 inside fixture mount 24. As FIG. 4A shows, fixture mount 24 includes separation line 111, which forms a weakened line for separation of proximal portion 24A from distal portion 24B of fixture mount 24.

FIG. 4B shows proximal fixture mount portion 24A separated from fixture mount distal portion 24B, leaving distal fixture mount portion 24B atop implant 10.

FIG. 4C shows comfort cap 112 positioned atop implant 10 and transfer mount portion 24B. Comfort cap 112 is closed at its proximal end 113, and includes a cylindrical opening at distal end 114, with flat shoulder 115 surrounding distal opening 114. Comfort cap 112 includes, on its inner surface, near opening 114, wholly or partly circumferential protrusion 116 that engages retentive groove 117 on fixture mount 24 when comfort cap 112 is placed atop portion 24B as shown in FIG. 4D.

FIGS. 5, 5A, 5B, 5C and 5D show vertical cross-sectional views of implant 10 with fixture mount 24 positioned above implant 10 (see FIG. 5) and fastener 104 positioned above, and then inside of fixture mount 24.

FIG. 5A shows proximal fixture mount 24 inserted into internal passage 16 of implant 10 with projection 25 seated in 6-sided internal female wrench-engaging surfaces 20.

FIG. 5B shows proximal fixture mount portion 24A separated from distal fixture mount portion 24B. See also, FIG. 4B.

FIG. 5C, like FIG. 4C, shows transfer cap 112 positioned atop fixture mount portion 24B, with portion 24B partly inside of implant 10.

FIG. 5C shows internal circumferential projection 116 on the inner surface of comfort cap 112 inside opening 114.

FIG. 5D shows comfort cap 112 in place atop implant 10 with flat shoulder 115, at its distal end, on shoulder 15 atop implant 10.

Figures 6, 6A, 6B, 7, 7A:
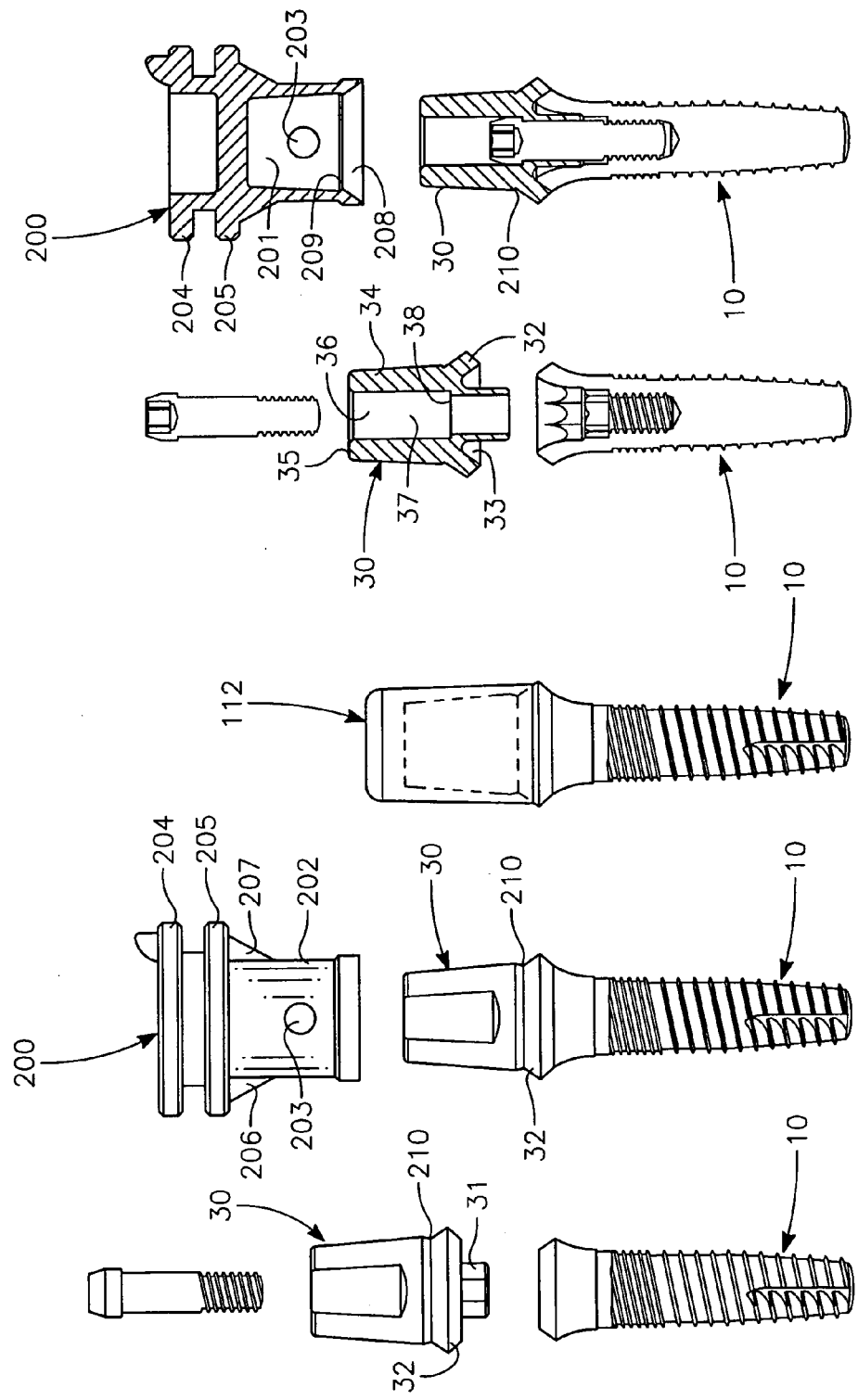
FIG. 6 shows the dental implant of FIG. 1, with an abutment, positioned above the implant and a fastener screw positioned above the abutment.
FIG. 6A shows the implant/abutment assembly of FIG. 6, with the abutment positioned atop the implant and with a snap-on transfer positioned above the implant/abutment assembly.
FIG. 6B shows the implant/abutment assembly of FIG. 6A, with a snap-on comfort cap in place atop the assembly.
FIG. 7 shows a side elevation view, in cross-section, of the implant, abutment and fastener of FIG. 6.
FIG. 7A shows a side elevation view, in cross-section, of the implant, abutment, and snap-on transfer of FIG. 6A.

FIGS. 6 and 7 show implant 10, with abutment 30 positioned above implant 10; FIGS. 6A, 6B and 7A, with abutment 30 in place atop implant 10. Abutment 30 includes distal, multi-sided, male wrench-engaging portion 31. Proximal to distal male portion 31 is distally projecting, circumferential-extending portion 32 that tapers downwardly, outwardly and distally to form circumferential groove 33. Atop circumferential flange or shoulder 32 is frusto-conical proximal portion 34. Portion 34 includes upper flat surface 35 surrounding opening 36 into an internal, distally-extending passage 37. Inside passage 37 is a shoulder or flange 38 that extends circumferentially around the inner surface of the passage.

FIGS. 6A and 7A show transfer 200, positioned above implant 10. Transfer 200 includes an internal, longitudinally extending passage 201. Transfer 200 also includes, on its external surface 202, circular openings 203, external circumferential flanges 204 and 205, and supports 206 and 207, all integrally formed with the transfer. Inside passage 201, near its distal opening 208, is circumferentially-extending protrusion 209 on the inner surface of passage 201. Protrusion 209 engages circumferentially-extending groove 210 on the external surface of abutment 30 when transfer 200 is placed atop abutment 30.

FIG. 6B shows implant 10 with abutment 30 in place atop implant 10 and with comfort cap 112 in place atop abutment 30. The retentive groove 116 inside comfort cap 112 engages groove 210.

The invention claimed is:

1. A fixture mount/abutment for engagement with, and for placement of an endosseous dental implant, and for conversion to an abutment after said placement, comprising:

a distal abutment portion and a proximal, separable fixture mount portion that includes a plurality of undercut regions distal to a plurality of external flanges, and that is joined to said abutment portion by a weakened area that facilitates separation of said fixture mount portion from said abutment portion, said distal abutment portion having at its distal end, a multi-sided male projection having a plurality of sides and a size and shape suitable for said engagement, said distal abutment portion including, proximal to said projection, a bevel or chamfer portion extending wholly or partly around said distal abutment portion, and proximal to said bevel or chamfer portion, a frusto-conical portion extending wholly or partly around said distal abutment portion, said frusto-conical portion including, on its outer surface, a wholly or partly circumferential groove for engaging a wholly or partly circumferential protrusion located on the inner surface of a snap-on transfer or snap-on comfort cap, and, at the proximal end of said abutment portion, said weakened area, and, proximal to said weakened area, said separable fixture mount portion comprising external, internal, or internal and external wrench-engaging surfaces to twist, turn or hold said fixture mount/abutment, said fixture mount/abutment including an internal, longitudinal through passage.

2. The fixture mount/abutment of claim 1 wherein said multi-sided male projection includes six or eight sides.

* * * * *